United States Patent
Nash

(10) Patent No.: US 10,085,859 B2
(45) Date of Patent: Oct. 2, 2018

(54) METHODS OF MANUFACTURING A DRUG-ELUTING STENT

(71) Applicant: Medtronic Vascular, Inc., Santa Rosa, CA (US)

(72) Inventor: Stephen Nash, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 1132 days.

(21) Appl. No.: 13/935,261

(22) Filed: Jul. 3, 2013

(65) Prior Publication Data
US 2015/0010422 A1    Jan. 8, 2015

(51) Int. Cl.
| A61F 2/86 | (2013.01) |
| B22F 5/10 | (2006.01) |
| A61L 31/16 | (2006.01) |
| A61L 31/02 | (2006.01) |
| A61L 31/14 | (2006.01) |
| B22F 3/24 | (2006.01) |

(52) U.S. Cl.
CPC .............. A61F 2/86 (2013.01); A61L 31/022 (2013.01); A61L 31/146 (2013.01); A61L 31/16 (2013.01); B22F 5/10 (2013.01); B22F 5/106 (2013.01); A61F 2240/005 (2013.01); B22F 2003/247 (2013.01); B22F 2005/103 (2013.01)

(58) Field of Classification Search
CPC ...... A61F 2/86; B22F 2005/103; B22F 5/106; A61L 31/16
See application file for complete search history.

(56) References Cited

U.S. PATENT DOCUMENTS

| 4,733,665 A | 3/1988 | Palmaz |
| 5,292,331 A | 3/1994 | Boneau |
| 5,421,955 A | 6/1995 | Lau |
| 5,935,162 A | 8/1999 | Dang |
| 6,730,116 B1 | 5/2004 | Wolinsky et al. |
| 8,052,744 B2 | 11/2011 | Girton |
| 8,381,774 B2 | 2/2013 | Mitchell et al. |
| 2011/0008405 A1* | 1/2011 | Birdsall et al. ............... 424/423 |
| 2011/0070357 A1 | 3/2011 | Mitchell et al. |

(Continued)

OTHER PUBLICATIONS

Banhart, John "Manufacture, Characterisation and Application of Cellular Metals and Metal Foams" Progress in Materials Science 46 (2001) 559-632.

*Primary Examiner* — Weiping Zhu
(74) *Attorney, Agent, or Firm* — Medler Ferro Woodhouse & Mills PLLC

(57) ABSTRACT

Methods for manufacturing an endovascular stent having channel(s) formed therein for containing a therapeutic material. A molding and sintering process forms a thin-walled tubular component having a tubular core structure encapsulated therein. Portions of the thin-walled tubular component are removed to form at least a portion of the endovascular stent in a pattern corresponding to that of the tubular core structure such that the tubular core structure or corresponding channel(s) left thereby are captured within a wall of the formed stent. The tubular core structure is removed to leave a corresponding channel(s) in its stead. A plurality of holes is formed in the stent wall for filling the stent channel(s) with the therapeutic material and for eluting the therapeutic material therefrom.

21 Claims, 10 Drawing Sheets

(56) References Cited

U.S. PATENT DOCUMENTS

2012/0067454 A1    3/2012   Melder
2012/0067455 A1    3/2012   Mitchell et al.
2012/0070562 A1    3/2012   Avelar et al.
2012/0070563 A1    3/2012   Mitchell et al.

\* cited by examiner

METHODS OF MANUFACTURING A DRUG-ELUTING STENT

FIELD OF THE INVENTION

The present invention relates to implantable medical devices that release a therapeutic material and methods of forming such medical devices.

BACKGROUND OF THE INVENTION

Drug-eluting implantable medical devices have become popular in recent times for their ability to perform their primary function (such as structural support) and their ability to medically treat the area in which they are implanted.

For example, drug-eluting stents have been used to prevent restenosis in coronary arteries. Drug-eluting stents may administer therapeutic agents such as anti-inflammatory compounds that block local invasion/activation of monocytes, thus preventing the secretion of growth factors that may trigger VSMC proliferation and migration. Other potentially anti-restenotic compounds include antiproliferative agents, such as chemotherapeutics, which include rapamycin and paclitaxel. Other classes of drugs such as anti-thrombotics, anti-oxidants, platelet aggregation inhibitors and cytostatic agents have also been suggested for anti-restenotic use.

Drug-eluting medical stents may be coated with a polymeric material which, in turn, is impregnated with a drug or a combination of drugs. Once the stent is implanted at a target location, the drug is released from the polymer for treatment of the local tissues. The drug is released by a process of diffusion through the polymer layer for biostable polymers, and/or as the polymer material degrades for biodegradable polymers.

Controlling the rate of elution of a drug from the drug impregnated polymeric material is generally based on the properties of the polymer material. However, at the conclusion of the elution process, the remaining polymer material in some instances has been linked to an adverse reaction with the vessel, possibly causing a small but dangerous clot to form. Further, drug impregnated polymer coatings on exposed surfaces of medical devices may flake off or otherwise be damaged during delivery, thereby preventing the drug from reaching the target site. Still further, drug impregnated polymer coatings are limited in the quantity of the drug to be delivered by the amount of a drug that the polymer coating can carry and the size of the medical devices. Controlling the rate of elution using polymer coatings is also difficult.

Bare metal, uncoated drug-eluting stents made from a hollow-tubular wire filled with a therapeutic material have been proposed. However, forming a hollow-wire stent by bending a hollow-wire into a stent form may cause kinking, cracking, or other undesirable properties in the finished stent. Accordingly, bare metal, uncoated drug-eluting stents are needed that utilize the advantages of a hollow-wire stent, such as the ability to delivery increased quantities of the therapeutic substance and improved control of the elution rate of the therapeutic substance, while reducing potential manufacturing difficulties of a hollow-wire stent.

BRIEF SUMMARY OF THE INVENTION

Embodiments described herein are directed to methods of manufacturing an endovascular stent from a generally cylindrical thin-walled tubular component formed by a molding and sintering process. The thin-walled tubular metal component is molded to encapsulate a tubular core structure having a stent pattern. Portions of the thin-walled tubular component are removed, such as by laser cutting or etching, to form at least a portion of the endovascular stent in the stent pattern of the tubular core structure, wherein the tubular core structure or a corresponding channel left thereby are captured within a wall of the formed stent. If the tubular core structure is captured within the wall of the formed stent it is subsequently removed to leave a corresponding channel within the wall of the stent in its stead. A plurality of holes are formed in the wall of the stent to access the channel or channels therein, with the plurality of holes being configured for filling a channel of the stent with a therapeutic material and for eluting the therapeutic material therefrom when the stent is deployed within a vessel.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 6AA is a cross-sectional view of a strut of the stent form of FIG. 6 in accordance with another embodiment.

DETAILED DESCRIPTION OF THE INVENTION

Specific embodiments of the present invention are now described with reference to the figures, wherein like reference numbers indicate identical or functionally similar elements. The stent in accordance with the disclosure may be either of a balloon-expandable type or a self-expanding type. The term "self-expanding" is used in the following description with reference to the prostheses hereof and is intended to convey that the structures are shaped or formed from a material that can be provided with a mechanical memory to return the structure from a radially compressed or constricted delivery configuration to an expanded deployed configuration. Non-exhaustive exemplary materials that are suitable for forming a prosthesis in accordance with embodiments hereof include titanium, 316L stainless steel, other low carbon chromium-nickel stainless steel, a pseudo-elastic metal such as a nickel titanium alloy (nitinol), or a so-called super alloy, which may have a base metal of nickel, cobalt, chromium, or other biocompatible metal. Mechanical memory may be imparted to a stent structure as described below by thermal treatment to achieve a spring temper in stainless steel, for example, or to set a shape memory in a susceptible metal alloy, such as nitinol.

The following detailed description is merely exemplary in nature and is not intended to limit the invention or the application and uses of the invention. Although the description of embodiments hereof are in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

Figure 1:
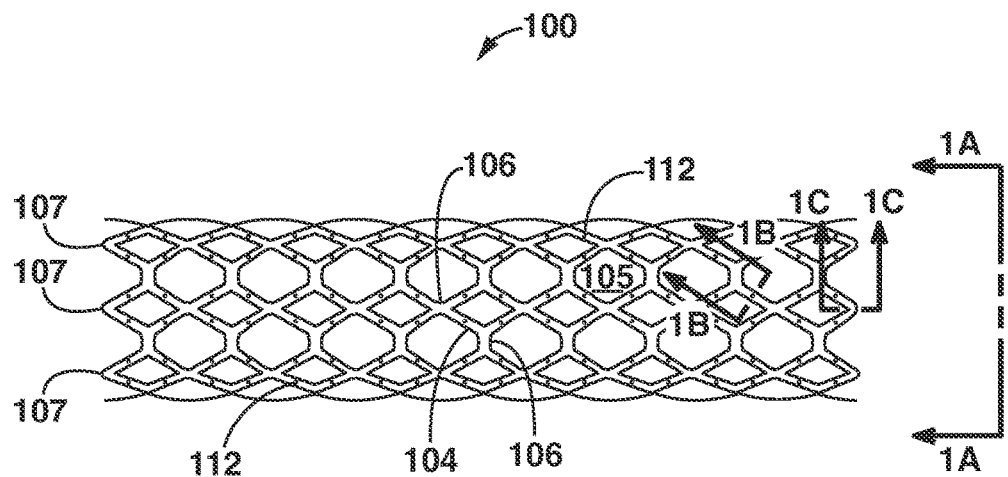
FIG. 1 is a side view of an endovascular stent formed in accordance with an embodiment hereof.

An endovascular stent 100 for delivering a therapeutic material within a vessel that may be formed by methods disclosed herein is shown in its deployed configuration in FIG. 1. More particularly, stent 100 may be a self-expanding endovascular prosthesis that is deformable or compressible into a reduced diameter delivery configuration (not shown) to be percutaneously deliverable to a treatment site within the vasculature via a delivery catheter (not shown), wherein stent 100 returns to an expanded or deployed configuration as shown in FIG. 1 upon release from the delivery catheter during deployment. With reference to the end view of stent 100 shown in FIG. 1A, stent 100 may be considered tubular or cylindrical with an inner or adluminal surface 101 that defines a blood flow lumen 102 therethrough and with an outer or abluminal surface 103 that sits in apposition with a vessel wall when stent 100 is deployed therein. Stent 100 has side openings 105 therethrough that are defined by generally straight segments or struts 104 and intersections or junctions 106, as shown in FIG. 1, such that stent 100 has a lattice-like or diamond pattern. Crowns or bends 107 join pairs of struts 104 at the ends of stent 100. In another embodiment (not shown), selected junctions 106 of stent 100 may be disconnected to form facing crowns so as to increase the flexibility of the stent. Stents formed in accordance with methods disclosed herein are not limited to the stent pattern shown in FIG. 1, and stent 100 may be formed into any stent pattern suitable for use as an endovascular stent. For example, and not by way of limitation, stent 100 can be formed into stent patterns disclosed in any of U.S. Pat. No. 4,733,665 to Palmaz, U.S. Pat. No. 5,292,331 to Boneau, U.S. Pat. No. 5,421,955 to Lau, U.S. Pat. No. 5,935,162 to Dang, and U.S. Pat. No. 6,730,116 to Wolinsky et al., each of which is incorporated by reference herein in its entirety.

Figure 1B:
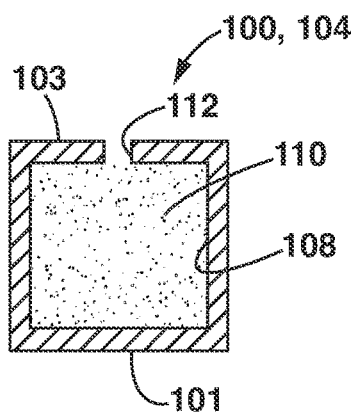
FIG. 1B is a cross-sectional view of a strut of the stent of FIG. 1 taken along line 1B-1B thereof.
Figure 1A:
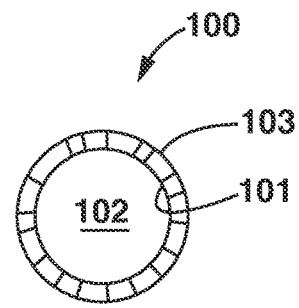
FIG. 1A is an end view of the stent of FIG. 1 taken in the direction of line 1A-1A thereof.
Figure 1C:
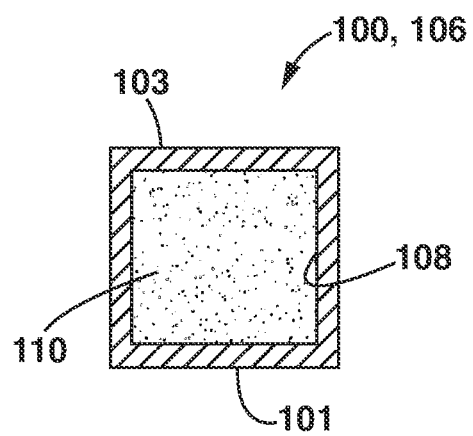
FIG. 1C is a cross-sectional view of a crown of the stent of FIG. 1 taken along line 1C-1C thereof.

FIG. 1B is an enlarged cross-sectional view of stent 100 taken along line B-B of FIG. 1 at a strut 104 and FIG. 1C is an enlarged cross-sectional view taken along line C-C of FIG. 1 at a crown 107. Stent 100 is formed to have a channel 108 extending within struts 104 and junctions 106 thereof, such that the struts, crowns and junctions, as well as stent 100, may be described as hollow or tubular, e.g. having a wall. In an embodiment, channel 108 extending within and between each of the struts 104 and junctions 106 of stent 100 may be described as a continuous channel. Channel 108 is shown in FIGS. 1B and 1C filled with a biologically or pharmacologically active therapeutic material 110.

Holes or apertures 112 are dispersed along the length of stent 100 to permit therapeutic material 110 to elute from channel 108. In the embodiment shown in FIG. 1, holes 112 are disposed in the abluminal surface 103 directed outwardly or toward the vessel wall when stent 100 is deployed therein. In another embodiment, holes 112 may be provided as well or alternatively in the adluminal surface 101 of struts 104. Holes 112 may be sized and shaped as desired to control the elution rate of therapeutic material 110 from stent 100 with larger sized openings generally permitting a faster elution rate and smaller sized openings generally providing a slower elution rate. Further, the size and/or quantity of holes 112 may be varied along the length of stent 100 in order to vary the quantity and/or rate of therapeutic material 110 being eluted from stent 100 at different portions of stent 100. In accordance with embodiments hereof, holes 112 may be, for example and not by way of limitation, 5-30 μm in diameter. Holes 112 may have a constant diameter through a wall of strut 104, as shown in FIG. 1B, or may have a tapered or conical shape.

Figure 1D:
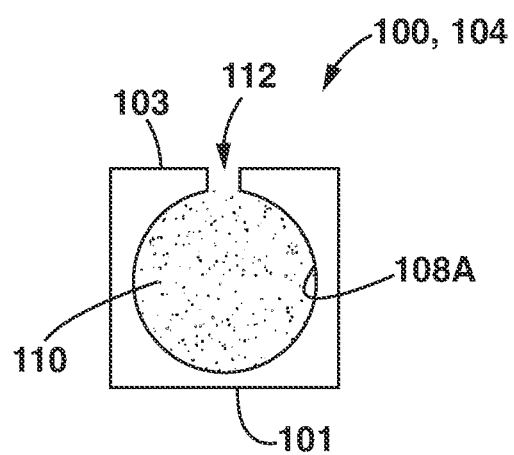
FIG. 1D is a cross-sectional view of a strut of the stent of FIG. 1 in accordance with another embodiment.
Figure 2:
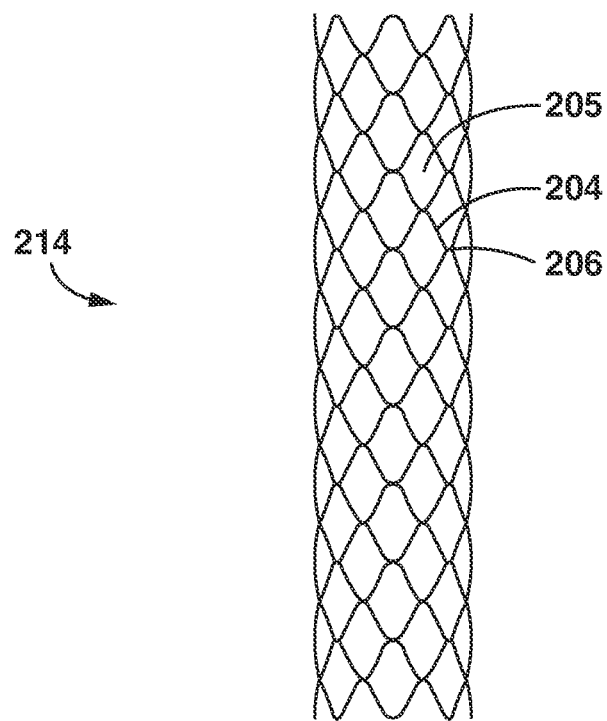
FIG. 2 is a side view of a tubular core structure in accordance with an embodiment hereof.
Figure 3:
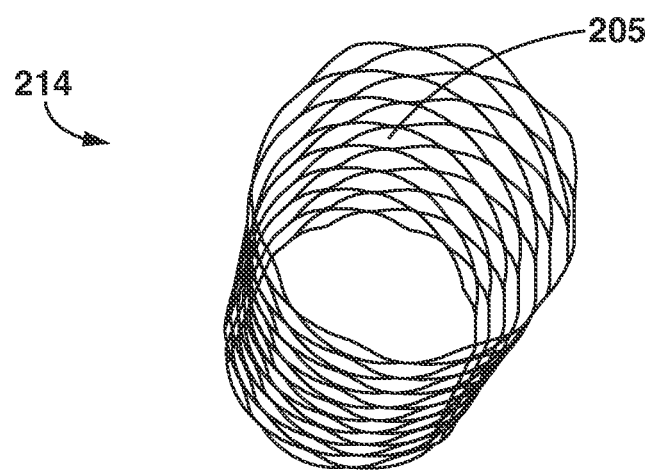
FIG. 3 is a perspective end view of the tubular core structure of FIG. 2.

A method of forming endovascular stent 100 for delivering therapeutic material 110 within a vessel is described with reference to FIGS. 2-6. A tubular core structure 214 for forming continuous channel 108 in stent 100 is shown in FIGS. 2 and 3. Tubular core structure 214 has a stent pattern with core side openings 205 therethrough that are defined by core struts 204 and core junctions 206 over which, or around which respective struts 104 and junctions 106 of stent 100 are to be formed respectively. In the embodiment of FIG. 2, tubular core structure 214 is a structure over which the entire stent 100 is formed such that the stent pattern of tubular core structure 214 serves as a template for the final stent pattern of stent 100. Tubular core structure 214 also functions as a space-holding or channel-holding geometry that corresponds to the geometry of channel 108 within stent 100. As such, core struts 204 and core junctions 206 of tubular core structure 214 may have any suitable cross-sectional shape, e.g. a substantially square cross-section for forming channel 108 as shown in FIGS. 1B and 1C or a circular cross-section for forming a channel 108A as shown in FIG. 1D. Tubular core structure 214 may be formed with a more complicated cross-sectional shape in accordance with other embodiments hereof for forming a channel within the struts, junctions and crowns of stent 100 with that corresponding cross-section. In embodiments hereof, tubular core structure 214 may be over-sized or made larger than a desired final dimension for channel 108 and stent 100 in order to account for shrinkage or compression of tubular core structure 214 that may occur during the molding and sintering process described below.

In embodiments hereof, tubular core structure 214 is made in a rapid prototyping or a molding process, and consists of a sacrificial material that will burn away during the sintering process or is otherwise extracted or removed, such as by being evaporated, eroded or dissolved after formation of the stent to leave a corresponding channel or space within the stent. As would be understood by one of ordinary skill in the art, a rapid prototyping process is a process of making a three-dimensional solid object of virtually any shape from a digital model and utilizes 3D printing technology in which the three-dimensional object is "printed" using an additive layering process until the object is complete. In embodiments hereof, a digital model of tubular core structure 214 is created and 3D printing technology is utilized in which successive layers of the sacrificial material are laid down until tubular core structure 214 is formed. Alternatively, the tubular core structure may be formed by molding processes such as compaction, compression or injection.

Suitable sacrificial materials for making tubular core structure 214 are, by way of example but not limited to, urea or a similar material that is erodible by an acid-based solvent, sodium chloride or a similar material dissolvable by a water-based solvent, or magnesium or a similar material removable by evaporation at a temperature below the temperature used during the sintering process. In accordance with other embodiments hereof, certain polymeric materials such as polyurethane are suitable as sacrificial materials for making tubular core structures 214 as these polymeric materials may also be evaporated at a temperature below the temperature used during the sintering process. Extraction of the tubular core component can occur during the sintering step or it can happen after the sintering step. It can occur in a pressure and temperature controlled environment.

Figures 4, 4A:
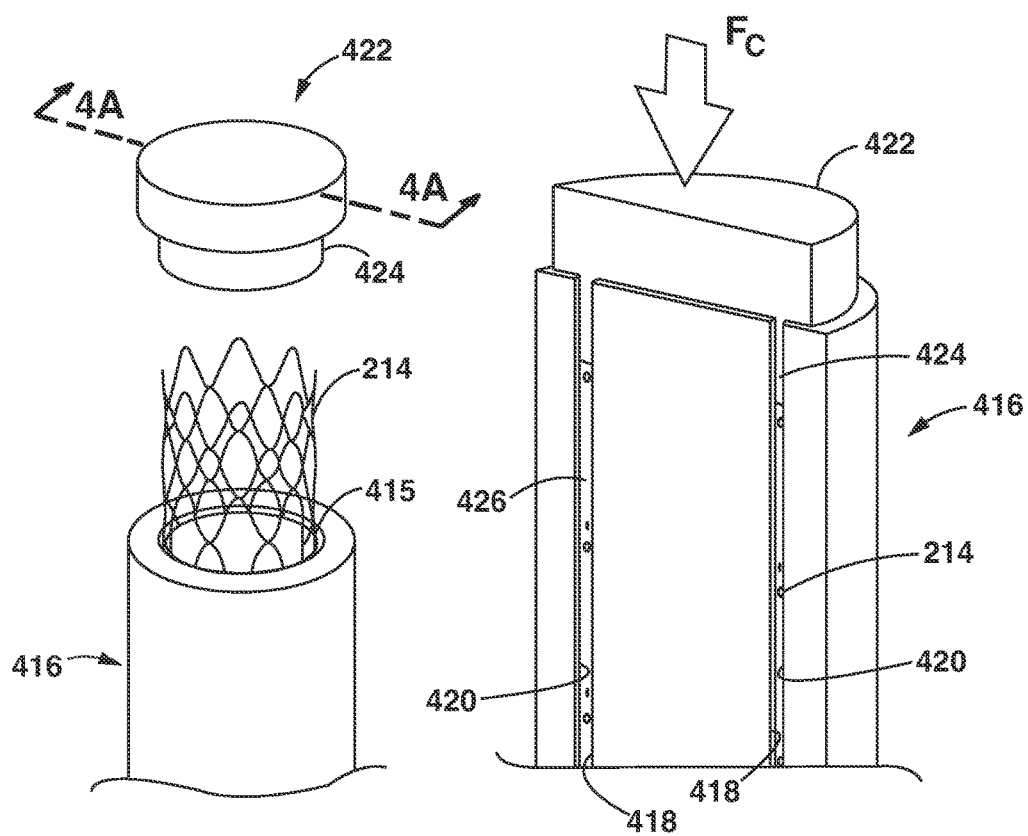
FIG. 4 is a perspective view of a molding apparatus in accordance with an embodiment hereof.
FIG. 4A is a longitudinal sectional view of the molding apparatus of FIG. 4 taken along line 4A-4A thereof.

With reference to FIGS. 4 and 4A, tubular core structure 214 is positioned within an annular mold cavity 415 of a mold 416, wherein the mold cavity 415 has a first or inner circumferential molding surface 418 for forming adluminal surface 101 of endovascular stent 100 and a second or outer circumferential molding surface 420 for forming abluminal surface 103 of stent 100. When disposed within mold 416, tubular core structure 214 is spaced apart from, and preferably centered between the first and second molding surfaces 418, 420 of mold cavity 415 so that tubular core structure 214 and channel 108 formed thereby will be substantially centered between the adluminal and abluminal surfaces 101, 103 of stent 100. In one example illustrated in FIG. 7, knobs 728 help to center core structure 714 between the first and second molding surfaces of a mold cavity. Mold 416 includes a compression cap 422 having an annular protrusion 424 that is sized to be received within mold cavity 415. Compression cap 422 is configured to receive a compressive force $F_C$ that is transferred via annular protrusion 424 to the contents within mold cavity 415 as described in more detail below. It should be understood by one of ordinary skill in the art that mold 416 with compression cap 422 are by way of example only and are not meant to limit use of methods herein to such a molding tool as various other compression molding arrangements may be adapted for use herein.

Metal particles 426 for forming stent 100 are placed, poured and/or packed within mold cavity 415 such that metal particles 426 fully surround and envelop core struts 204 and core junctions 206 of tubular core structure 214 and fill core side openings 205. Magnetic, ultrasound or vibrational energy may be employed to ensure that the particles are settled around the tubular structure. Metal particles 426 may be sized as may be typical for metal injection molding (MIM), such as ultra-fine particles having an average size of around 5 µm, fine particles having an average size of around 10 µm, or larger particles up to around 200 µm is size. Suitable metal particles for forming stent 100 in accordance with methods herein include particles of the exemplary metals listed above.

In another embodiment, tubular core structure 214 may be coated with metal particles 426 prior to positioning tubular core structure 214 within mold cavity 415. Metal particles 426 may be applied to tubular core structure 214 by spraying, dipping, mixing, and/or brushing, and tubular core structure 214 so coated with metal particles 426 may then be disposed within mold 416 for further processing as described below. A binder material such as polyvinyl alcohol may be used to adhere the metal particles to the tubular core structure 214.

Figure 5:
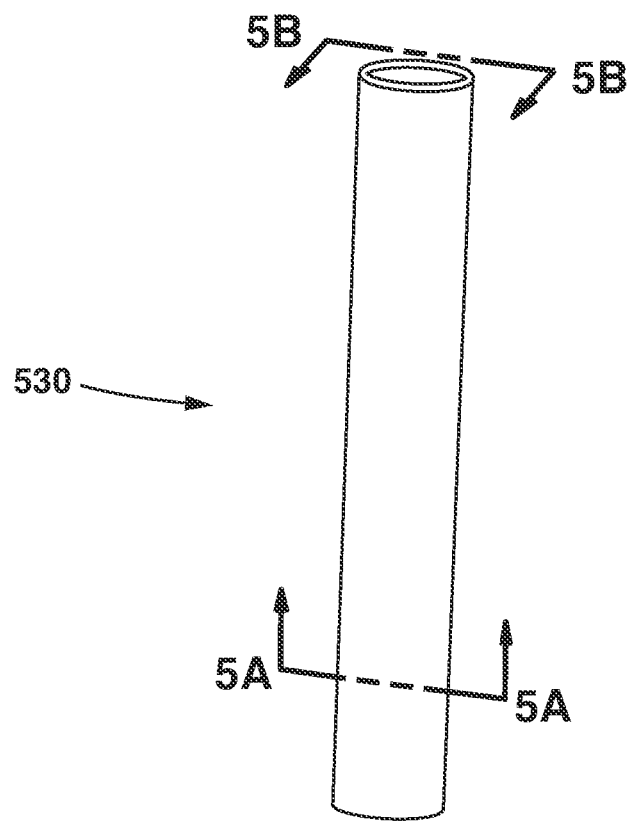
FIG. 5 is a perspective side view of a metallic tubular component in accordance with an embodiment hereof.

With reference to FIG. 4A, compressive force $F_C$ applied to cap 422 is converted to a mold pressure applied by annular protrusion 424 to the contents of mold cavity 415, which includes tubular core structure 214 and metal particles 426, to press together metal particles 426 to form a cold weld therebetween. More particularly, as will be understood by those familiar with powder metallurgy, compressive force $F_C$ is of a sufficient magnitude to create a mold pressure such that a cold weld bonds metal particles 426 together. FIG. 5 shows the resulting formed metallic tubular component 530, removed from mold 416 and encapsulating tubular core structure 214 therewithin. In powder metallurgy embodiments hereof, cold-welding is utilized as a bonding process where metal particles 426 are combined to form metallic tubular component 530 through means of intense pressure that does not rely on heat to change the state of the metal particles being bonded, which means metal particles 426 remain in a solid state throughout the process. It is believed that during the cold-welding process, deformities occur across 60 to 80% of the bonding surface of metal particles 426, and this allows permanent bonding to take place on the atomic level therebetween. A suitable pressure for forming a cold weld between the individual metal particles is material and particle size dependent, wherein metal particles 426 of a cobalt-chromium alloy or stainless steel 316L may require a different compressive force $F_C$ to achieve a cold weld between metal particles thereof, with smaller particle sizes of either material generally requiring less pressure for forming cold welds therebetween. A suitable pressure also depends on a volume of the mold cavity 415 and a volume of metal particles 426 therein. In an embodiment hereof, a suitable compressive force $F_C$ or pressure to cold weld metal particles in the size range of 10-100 µm to form a stent having a 10 mm outer diameter and a 20 mm height may range from 1 to 50 tons.

Figure 5A:
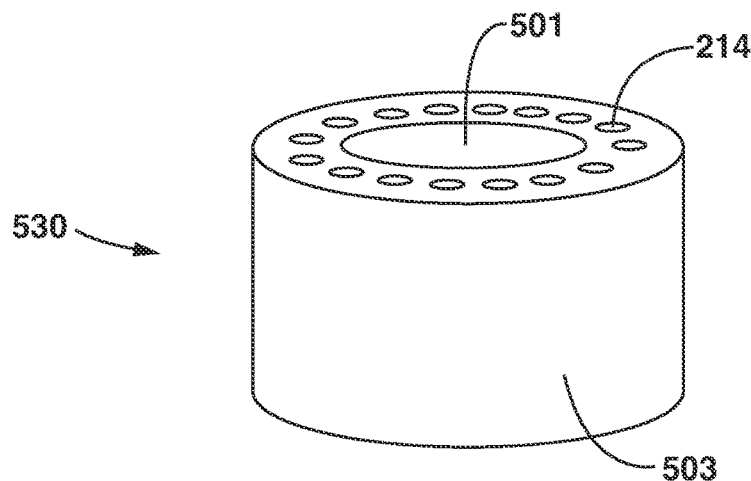
FIG. 5A is a transverse perspective cross-sectional view of a portion of the metallic tubular component shown in FIG. 5 taken along line 5A-5A.
Figure 5B:
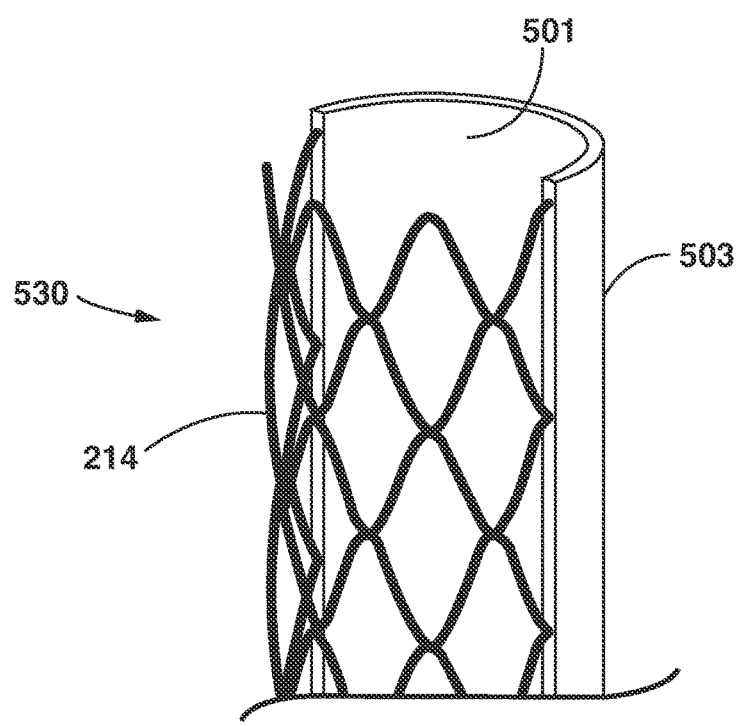
FIG. 5B is a partial longitudinal sectional view of a portion of the metallic tubular component shown in FIG. 5 taken along line 5B-5B thereof.

Metallic tubular component 530 created during the cold-welding process is then sintered to form a solid wall metal tube having smooth interior and exterior surfaces 501, 503 between which either tubular core structure 214 or a continuous channel 108 in the stent pattern of tubular core structure 214 is encased. Accordingly after the sintering step in an embodiment hereof, tubular core structure 214 may remain between interior and exterior surfaces 501, 503 of metallic tubular component 530, as best shown in the cross-sectional and sectional views of a portion of metallic tubular component 530 that are shown in FIGS. 5A and 5B, respectively. In another embodiment, tubular core structure 214 may burn away or evaporate during the sintering step such that continuous channel 108 in the stent pattern of tubular core structure 214 is encased or defined between interior and exterior surfaces 501, 503 of metallic tubular component 530. As would be understood by one of ordinary skill in the art, sintering of metallic tubular component 530 is carried out in an appropriate furnace that provides an operator control over heating rate, time, temperature and an atmosphere/environment thereof.

A suitable sintering temperature for use in embodiments hereof is in general the temperature at which a metal particle connects through its boundaries and merges with other metal particles so as to form a larger metal particle, with enough heat being applied for the metal particles to melt at the points where they have formed a cold weld. A sintering temperature is material and particle size dependent and is related to the material's melting point. In general a sintering temperature may be considered to be two-thirds of a melting point of that material, and in some instances is a temperature just below the melting point. In methods hereof once metallic tubular component 530 is brought to a suitable temperature for sintering the metal particles from which it is formed, the atoms in the metal particles cold welded together diffuse across the boundaries of the individual metal particles to thereby fuse them together such that metallic tubular component is further solidified and strengthened. In an embodiment in which metal particles 426 are of 316L stainless steel, which has a melting point of approximately 1400 degrees centigrade, a sintering temperature of approximately 1100 degrees centigrade would be appropriate for sintering the cold-welded particles thereof, with a sintering temperature in the range of 1000 to slightly under 1400 degrees centigrade also being suitable. Accordingly during formation of metallic tubular component 530, metal particles 426 do not intermingle or mix with the material of tubular core structure 214 and do not form bonds or otherwise react with the material of tubular core structure 214. Also post sintering, metallic tubular component 530 has a solid non-porous metallic wall within which one of tubular core structure 214 or continuous channel 108 are enclosed. By the use of "solid" to describe a wall of metallic tubular component 530 it is meant that the wall is substantially nonporous after the molding and sintering steps described above, such that a stent formed therefrom will have a nonporous wall surrounding channel 108 except where holes, such as drug loading and delivery holes 112, are formed therein.

Figure 6:
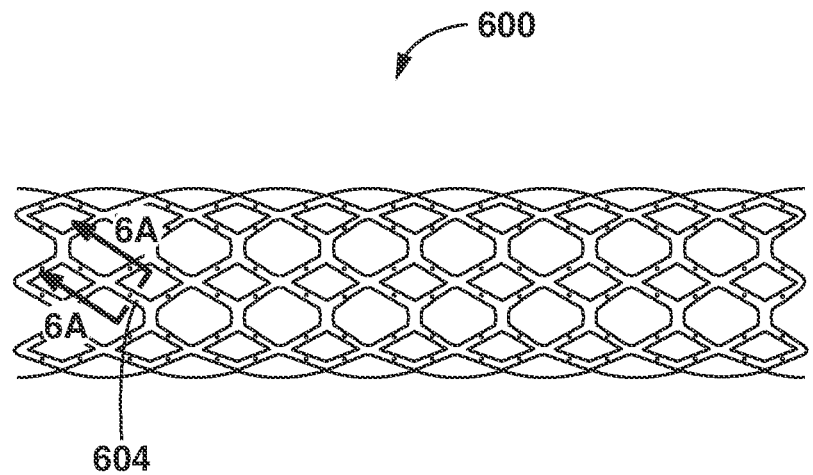
FIG. 6 is a side view of a stent form in accordance with an embodiment hereof.
Figure 6A:
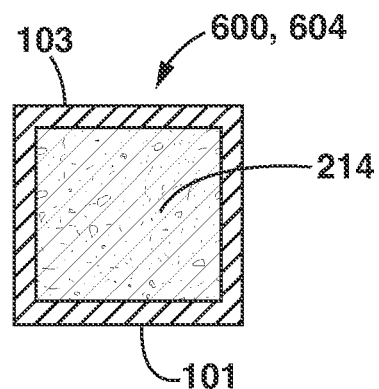
FIG. 6A is a cross-sectional view of a strut of the stent form of FIG. 6 taken along line 6A-6A thereof.
Figure 6A:
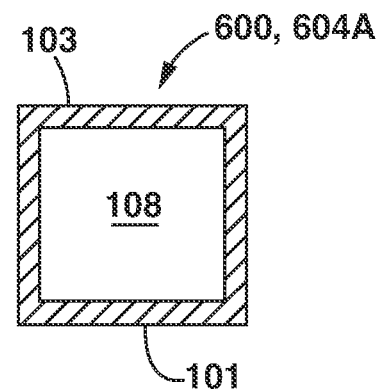

Post sintering, metallic tubular component 530 is cut to remove portions of the solid wall thereof to create a stent form 600 in the stent pattern of tubular core structure 214, as shown in FIG. 6. Care is taken during the cutting of metallic tubular component 530 to create side openings 105 without cutting the tubular core structure 214, as shown in the cross-section of stent form strut 604 in FIG. 6A. If the tubular core structure 214 is burned away during sintering, care is taken while forming side openings 105 to avoid cutting into the continuous channel 108 left thereby, as shown in the cross-section of an alternate stent form strut 604A in FIG. 6AA. Depending on the material selected for the tubular core structure, there may be some residual artifacts of the core structure left after the sintering step. In this case, a cleaning process can be employed afterward. Alternatively, the residual artifacts can be removed using pressure or a vacuum. In an embodiment, removing portions of the solid wall of metallic tubular component 530 includes laser cutting around the stent pattern of the tubular core structure 214, such that tubular core structure 214 serves as a guide or template in creating stent form 600 in the same pattern as tubular core structure 214. In another embodiment, in which the tubular core structure 214 is burned away during sintering, removing portions of the solid wall of metallic tubular component 530 includes laser cutting around continuous channel 108 that is in the stent pattern of tubular core structure 214, such that continuous channel 108 serves as a guide or template in creating stent form 600 in the same pattern as tubular core structure 214. In embodiments hereof in order to visualize tubular core structure 214 or continuous channel 108 such that one or the other may be used to guide the cutting and removing process, an x-ray may be used to distinguish between the less dense tubular core structure 214 or continuous channel 108 and the remaining material of metallic tubular component 530.

In an embodiment hereof with reference to FIGS. 1, 1B, 1D, and 6 a plurality of holes 112 are formed through the abluminal surfaces 103 of stent form struts 604 to provide access to tubular core structure 214. Tubular core structure 214 is then extracted from stent form 600 via the plurality of holes 112 to leave corresponding channel 108 in its stead or place, such that stent 100 is thereby formed. In various embodiments hereof, tubular core structure 214 is extracted from stent form 600 by eroding or dissolving the sacrificial material thereof using a suitable solvent as described above. This extraction step can occur in a controlled temperature and/or pressure environment, e.g. such as under vacuum or in a hydrogen atmosphere. However, it may not always be necessary to perform core extraction in a temperature and pressure controlled environment. Rather, this step may occur at room temperature and standard air conditions. In another embodiment hereof in which the tubular core structure 214 is burned away during sintering with reference to FIGS. 1, 6, and 6AA, a plurality of holes 112 are formed through the abluminal surfaces 103 of stent form struts 604 to provide access to channel 108, such that stent 100 is thereby formed. In embodiments hereof, holes 112 may be formed by any suitable process as would be apparent to one of ordinary skill in the art to include, by way of example and not limitation, laser drilling or etching the holes through the surface of stent form 600.

Figure 7:
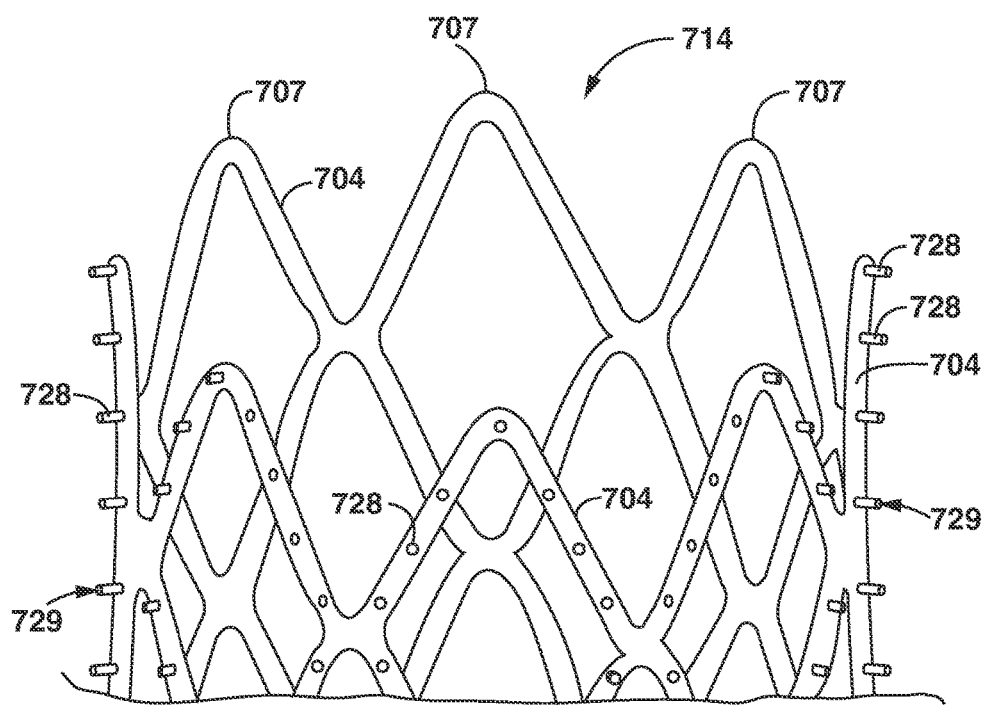
FIG. 7 is an enlarged view of an end portion of a tubular core structure in accordance with another embodiment.

FIG. 7 is an enlarged perspective view of an end portion of a tubular core structure 714 having core struts 704 and core crowns 707 in accordance with another embodiment hereof. Core struts 704 of tubular core structure 714 include knobs 728 that extend radially outward therefrom. When tubular core structure 714 is disposed within mold cavity 415 of mold 416, end surfaces 729 of knobs 728 will sit against outer circumferential molding surface 420. Metal particles 426 will be disposed around knobs 728 as well as the remaining portions of tubular core structure 714 in accordance with the methods described above such that after molding and sintering steps are performed, knobs 728 will extend through a solid wall of metallic tubular component 530. Subsequent removal of tubular core structure 714 by one of the methods described above will simultaneously leave a plurality of holes 112 formed by corresponding knobs 728, as well as a corresponding channel formed by core structure 714. Alternatively if tubular core structure 714 is burned away or evaporated during the sintering step, holes 112 will extend through the wall of metallic tubular component 530 at the former locations of knobs 728 without further processing. Accordingly, knobs 728 of tubular core structure 714 are configured to mold the plurality of holes 112 extending from the abluminal surface 103 through the strut wall of stent 100, thereby eliminating the need for performing a separate process step for forming the plurality of holes. Although four knobs 728 are shown on each core strut 704 of tubular core structure 714 for forming a corresponding number of holes 112, it should be understood that this is by way of example and not limitation and that any number of knobs 728 may be included for forming a corresponding number of holes 112. In another embodiment (not shown), knobs 728 may be provided, as well or alternatively, extending inwardly from core struts 704 toward a lumen of tubular core structure 714 or toward an opposing core strut 704 without departing from the scope hereof for forming corresponding holes 112 through strut walls of the final stent. Knobs 728 may be sized and shaped such that corresponding holes 112 formed thereby provide a desired elution rate of therapeutic material 110. Further, the size, quantity and/or shape of knobs 728 for forming holes 112 may be varied along the length of stent 100 in order to vary the quantity and/or rate of therapeutic material 110 being eluted from stent 100 at different portions of stent 100.

Channel 108 as formed by one of the methods described above is then filled with therapeutic material 110 via the plurality of holes 112, such that stent 100 is ready for delivering therapeutic material 110 within a vessel wherein the therapeutic material will be released from channel 108 via the plurality of holes 112.

Figure 8:
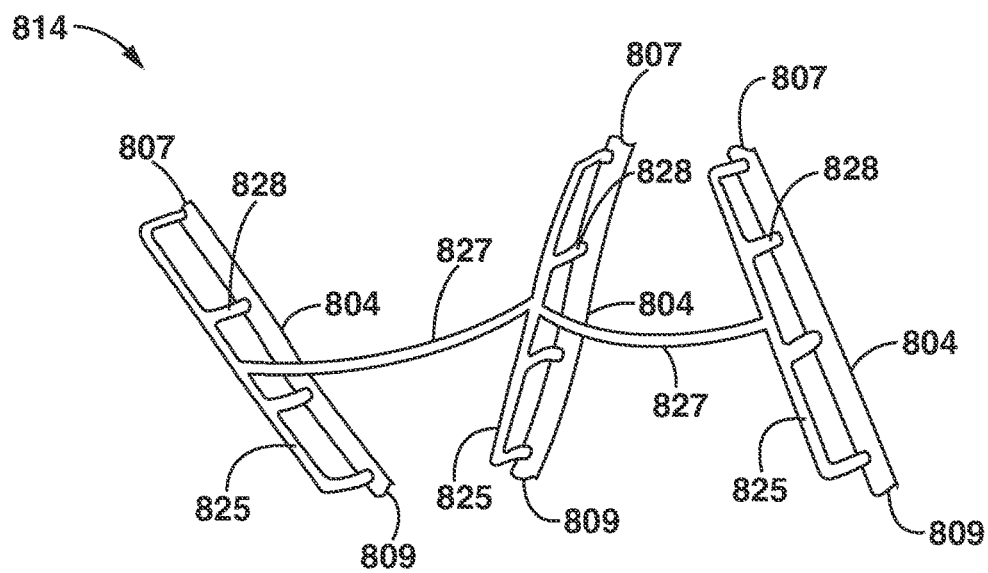
FIGS. 8 and 9 are perspective views of portions of a tubular core structure in accordance with another embodiment hereof.
Figure 9:
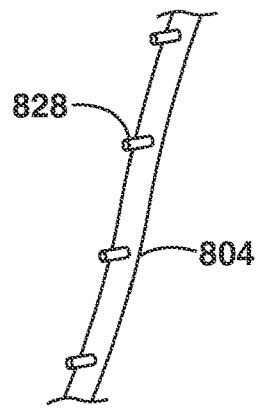
Figure 11:
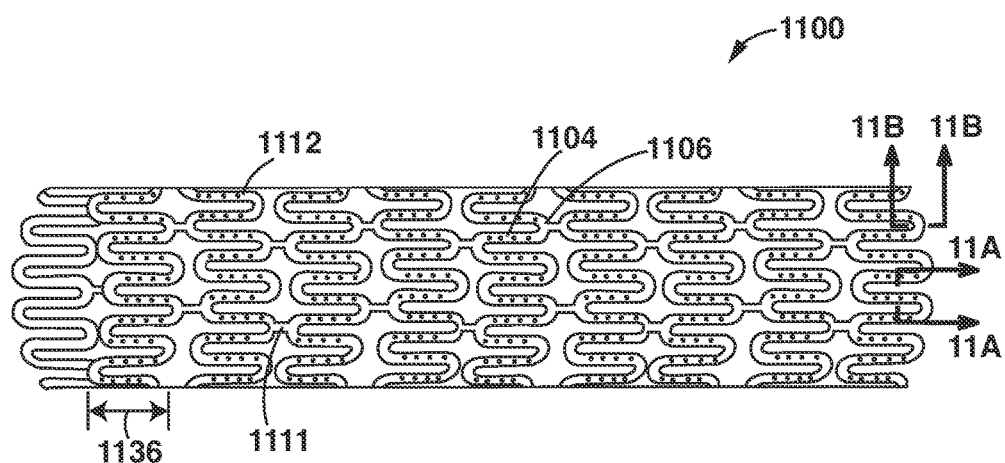
FIG. 11 is a perspective side view of an endovascular stent formed in accordance with another embodiment hereof.
Figures 11A, 11B:
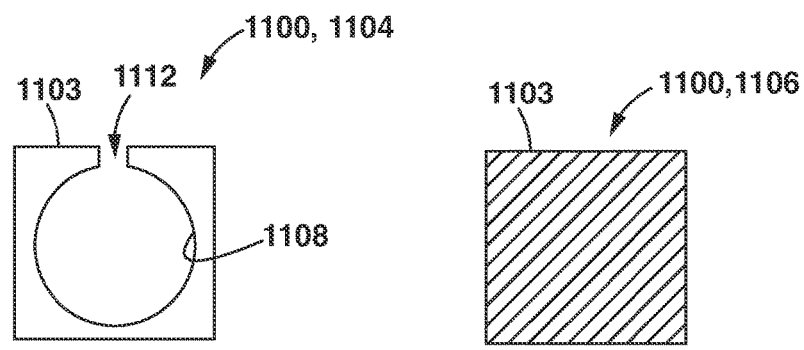
FIG. 11A is a cross-sectional view of a strut of the stent of FIG. 11 taken along line 11A-11A thereof.
FIG. 11B is a cross-sectional view of a crown of the stent of FIG. 11 taken along line 11B-11B thereof.

In another embodiment shown in FIGS. 8 and 9, a core structure 814 is disclosed that has a space holding geometry for forming a series of unconnected, separate channels 1108 within a stent 1100, as shown in FIGS. 11, 11A and 11B. Core structure 814 is a series of core struts 804 with an attachment member 825 extending parallel to each core strut and being spaced from and attached thereto by a plurality of knobs 828. Each attachment member 825 is disposed along a radially outward-facing surface of a core strut 804. An attachment member 825 of each core strut 804 is joined to the attachment member 825 of an adjacent core strut 804 by a band 827, such that the series of core struts 804 are banded together to form a tubular shape of core structure 814 over which a ring or circular segment 1136 of struts 1104 of stent 1100 is to be formed. In the embodiment of FIG. 8, core struts 804 are disposed at an angle with respect to a longitudinal axis of core structure 814 such that a first end 807 of each core strut 804 is disposed toward a respective first end 807 of the core strut 804 on one side thereof and a second end 809 of each core strut 804 is disposed toward a respective second end 809 of the core strut 804 on the other side thereof.

Figure 10:
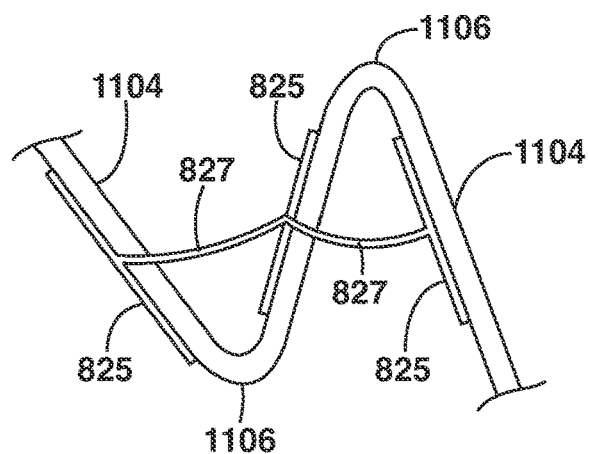
FIG. 10 is a perspective view of an end portion of a stent during formation in accordance with an embodiment hereof.

A plurality of core structures 814 are loaded within a mold, such as mold 416, and metal particles are added thereto. A pressure is applied to the contents of the mold to cold weld the metal particles together and thereby form a metallic tubular component that is then sintered, as described above. Portions of the metallic tubular component are then removed, by laser cutting for example, to form the stent pattern of stent 1100 shown in FIG. 11. With reference to FIG. 10, attachment members 825 and bands 827 are embedded within an external surface of the metallic tubular component after the molding and sintering process and are removed after formation of stent 1100 by either an erosion or dissolution process used to extract core structure 814 from stent 1100 or by an abrasion process performed prior to the extraction of core structure 814. In an alternate embodiment, attachment members 825 and bands 827 are removed by an abrasion or erosion process applied to the metallic tubular component prior to cutting the pattern of stent 1100. In another embodiment, core structures 814 may burn off or evaporate during the sintering process eliminating the need for further processing to remove the attachment member and band structures from the metallic tubular component or stent 1100. Accordingly each core strut 804 of core structure 814 so described is configured to form a separate, individual channel 1108 and holes 1112 attendant thereto within a corresponding strut 1104 of stent 1100, as shown in FIG. 11A, with crowns 1106 that extend between adjacent struts 1104, as well as connector segments 1111 of stent 1100, having solid cross-sections as shown in FIG. 11B. Channels 1108 of stent 1100 are then filled with a therapeutic material via the plurality of holes 1112 in the abluminal surface 1103 of stent 1100, such that stent 1100 is ready for delivering the therapeutic material within a vessel wherein the therapeutic material will be released from channels 1108 via the plurality of holes 1112.

In accordance with embodiments hereof, channels 108, 1108 of stents 100, 1100 may be filled with a therapeutic material by methods described in U.S. Pat. Appl. Pub. No. 2011/0070357 to Mitchell et al, U.S. Pat. Appl. Pub. No. 2012/0070562 to Avelar et al, U.S. Pat. Appl. Pub. No. 2012/0067455 to Mitchell et al, U.S. Pat. Appl. Pub. No. 2012/0070563 to Mitchell et al, U.S. Pat. Appl. Pub. No. 2012/0067454 to Mitchell et al., and U.S. Pat. No. 8,381,774 to Mitchell et al, each of which is incorporated by reference herein in its entirety, or any other suitable method known to one of ordinary skill in the art.

Further processing of the stents in the above-described embodiments, such as annealing, cleaning, and other processes known to one of ordinary skill in the art, can be performed at appropriate times in the methods described above. For example, and not by way of limitation, annealing the stent may take place before filling the stent with the therapeutic material if the annealing step may damage the therapeutic material. Similarly, a final cleaning step may occur after filling the stent with the therapeutic material. Further, holes used to allow an etchant or dissolvent access to the tubular core structure for removal and/or used to fill the channels with a therapeutic material may be closed to control the elution rate and elution time of the therapeutic material from the stent.

The term "therapeutic material" refers to any biologically or pharmacologically active substance, whether synthetic or natural, that has a pharmacological, chemical, or biological effect on the body or a portion thereof. Suitable therapeutic materials that can be used in embodiments hereof include without limitation glucocorticoids (e.g. dexamethasone, betamethasone), antithrombotic agents such as heparin, cell growth inhibitors, hirudin, angiopeptin, aspirin, growth factors such as VEGF, antisense agents, anti-cancer agents, anti-proliferative agents, oligonucleotides, antibiotics, and, more generally, antiplatelet agents, anti-coagulant agents, antimitotic agents, antioxidants, antimetabolite agents, and anti-inflammatory agents may be used. Antiplatelet agents can include drugs such as aspirin and dipyridamole. Aspirin is classified as an analgesic, antipyretic, anti-inflammatory and antiplatelet drug. Dipyridamole is a drug similar to aspirin in that it has anti-platelet characteristics. Dipyridamole is also classified as a coronary vasodilator. Anticoagulant agents may include drugs such as heparin, protamine, hirudin and tick anticoagulant protein. Anti-cancer agents may include drugs such as taxol and its analogs or derivatives. Taxol is also classified as a cell-growth inhibitor. Antioxidant agents may include probucol. Anti-proliferative agents may include drugs such as amlodipine, doxazosin, and sirolimus (rapamycin) or other limus family compounds. Antimitotic agents and antimetabolite agents may include drugs such as methotrexate, azathioprine, vincristine, vinblastine, 5-fluorouracil, adriamycin and mutamycin. Antibiotic agents can include penicillin, cefoxitin, oxacillin, tobramycin, and gentamicin. Suitable antioxidants include probucol. Also, genes or nucleic acids, or portions thereof may be used. Such genes or nucleic acids can first be packaged in liposomes or nanoparticles. Furthermore, collagen-synthesis inhibitors, such as tranilast, may be used.

The stents described herein may be used conventionally to support blood vessels of the body after an angioplasty procedure. It is known that certain therapeutic materials eluted from stents may prevent restenosis or other complications associated with angioplasty or stent implantation. The stents described herein may alternatively be used in other organs or tissues of the body for delivery of drugs to treat tumors, inflammation, nervous conditions, or other conditions that would be apparent to those skilled in the art.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of forming an endovascular stent for delivering a therapeutic material within a vessel comprising the steps of:
    positioning a tubular core structure in a mold, wherein the tubular core structure has a pattern around which at least a portion of the endovascular stent is to be formed;
    placing metal particles in the mold around the tubular core structure;
    applying a force to press together the metal particles and create a solid wall metallic tubular component, wherein the tubular core structure is encased within the solid wall of the metallic tubular component;
    sintering the metallic tubular component to further solidify the component; and
    removing portions of the solid wall of the metallic tubular component to form at least a portion of the endovascular stent in the pattern of the tubular core structure.

2. The method of claim 1, wherein during the step of removing portions of the solid wall of the metallic tubular component the tubular core structure is captured within a wall of the endovascular stent.

3. The method of claim 2, wherein the tubular core structure extends within each strut and crown of the endovascular stent and the method further comprises the step of removing the tubular core structure from the struts and crowns to form a continuous channel in the pattern of the tubular core structure within the stent.

4. The method of claim 3, wherein prior to the step of removing the tubular core structure a plurality of holes are formed within the wall of the endovascular stent to provide access to the tubular core structure therein.

5. The method of claim 4, wherein the step of removing the tubular core structure includes eroding or dissolving the tubular core structure out of the plurality of holes.

6. The method of claim 4, wherein the plurality of holes are formed within an abluminal surface of the endovascular stent.

7. The method of claim 4, further comprising the step of:
    filling the continuous channel within the wall of the endovascular stent with the therapeutic material via the plurality of holes.

8. The method of claim 1, wherein during the step of sintering the metallic tubular component the tubular core structure burns away and forms a continuous channel in the pattern of the tubular core structure within the wall of the metallic tubular component.

9. The method of claim 8, wherein during the step of removing portions of the solid wall of the metallic tubular component the continuous channel in the pattern of the tubular core structure is captured within a wall of the endovascular stent.

10. The method of claim 9, further comprising the steps of:
    forming a plurality of holes through the wall of the endovascular stent to provide access to the continuous channel therein; and
    filling the continuous channel within the wall of the endovascular stent with the therapeutic material via the plurality of holes.

11. The method of claim 1, wherein the tubular core structure extends within struts of the endovascular stent and the method further comprises the step of removing the tubular core structure from the struts to form a separate channel in each strut.

12. The method of claim 1, further comprising the step of:
    creating the tubular core structure in a 3D printing or molding process prior to the step of positioning the tubular core structure in the mold.

13. The method of claim 1, wherein the mold has a first molding surface for forming an abluminal surface of the endovascular stent and a second molding surface for forming an adluminal surface of the endovascular stent and the tubular core structure is substantially centered between the first and second molding surfaces during the step of positioning the tubular core structure in the mold.

14. The method of claim 1, wherein the metal particles are selected from the group consisting of low carbon chromium-nickel stainless steel particles and cobalt chromium alloy particles.

15. The method of claim 1, wherein the step of applying a force includes axially compressing the metal particles and the tubular core structure.

16. The method of claim 1, wherein the of step of removing portions of the solid wall of the metallic tubular component includes laser cutting around the pattern of the tubular core structure within the solid wall of the metallic tubular component to form the endovascular stent in the pattern of the tubular core structure.

17. A method of forming an endovascular stent for delivering a therapeutic material within a vessel comprising the steps of:
    coating with metal particles a tubular core structure having a stent pattern around which the endovascular stent is to be shaped;
    disposing the coated tubular core structure within a mold;
    applying a force to press together the metal particles coated on the tubular core structure to create a metallic tubular component having a solid wall within which the tubular core structure is disposed;
    sintering the metallic tubular component; and
    forming the metallic tubular component into the endovascular stent by cutting around the stent pattern of the tubular core structure and removing portions of the solid wall of the metallic tubular component.

18. The method of claim 17, further comprising the steps of:
- forming a plurality of holes through a wall of the endovascular stent to provide access to the tubular core structure therein;
- removing the tubular core structure via the plurality of holes to leave a corresponding channel within the wall of the endovascular stent; and
- filling the channel with the therapeutic material via the plurality of holes.

19. The method of claim 17, wherein during the step of sintering the metallic tubular component the tubular core structure burns away and forms a corresponding channel in the stent pattern of the tubular core structure within the wall of the metallic tubular component.

20. The method of claim 19, wherein during the step of forming the metallic tubular component into the endovascular stent the channel in the stent pattern of the tubular core structure is captured within a wall of the endovascular stent.

21. The method of claim 20, further comprising the steps of:
- forming a plurality of holes through the wall of the endovascular stent to provide access to the channel therein; and
- filling the channel with the therapeutic material via the plurality of holes.

\* \* \* \* \*